(12) United States Patent
Janetzko et al.

(10) Patent No.: US 9,778,255 B2
(45) Date of Patent: Oct. 3, 2017

(54) ASSEMBLY FOR SELECTIVELY PERFORMING A CLINICAL CHEMISTRY TEST OR AN ELISA ASSAY, USE OF SAID REAGENT CARTRIDGE AND ASSEMBLY

(71) Applicants: Alfred Janetzko, Butzbach (DE); Wilhelm Sänger, Wilnsdorf (DE); Cyril E. Geacintov, Mountainside, NJ (US)

(72) Inventors: Alfred Janetzko, Butzbach (DE); Wilhelm Sänger, Wilnsdorf (DE); Cyril E. Geacintov, Mountainside, NJ (US)

(73) Assignee: DRG Instruments GMBH, Marburg, DE (US)

( * ) Notice: Subject to any disclaimer, the term of this patent is extended or adjusted under 35 U.S.C. 154(b) by 272 days.

(21) Appl. No.: 14/453,978

(22) Filed: Aug. 7, 2014

(65) Prior Publication Data

US 2014/0377785 A1    Dec. 25, 2014

Related U.S. Application Data

(63) Continuation of application No. 13/503,276, filed as application No. PCT/EP2010/063732 on Sep. 17, 2010, now abandoned.

(30) Foreign Application Priority Data

Oct. 30, 2009    (DE) .................. 10 2009 051 428

(51) Int. Cl.
*B01L 1/00* (2006.01)
*B01L 3/00* (2006.01)
*G01N 33/543* (2006.01)

(52) U.S. Cl.
CPC ........ *G01N 33/54386* (2013.01); *B01L 3/508* (2013.01); *B01L 2200/16* (2013.01); *B01L 2300/0609* (2013.01)

(58) Field of Classification Search
CPC ............... G01N 33/54386; B01L 3/508; B01L 2200/16; B01L 2300/0609
USPC ...................................... 435/287.2
See application file for complete search history.

(56) References Cited

U.S. PATENT DOCUMENTS

| | | | | |
|---|---|---|---|---|
| 4,608,231 | A * | 8/1986 | Witty | B01L 3/502 206/569 |
| 5,482,861 | A * | 1/1996 | Clark | B01L 3/08 422/63 |
| 2002/0164779 | A1 * | 11/2002 | Cocola | B01L 3/50855 435/287.2 |
| 2002/0164826 | A1 * | 11/2002 | Braach-Maksvytis | G01N 33/54366 436/548 |
| 2006/0120926 | A1 * | 6/2006 | Takada | B01L 3/50853 422/400 |

* cited by examiner

*Primary Examiner* — Nathan Bowers
(74) *Attorney, Agent, or Firm* — Fox Rothschild LLP

(57) ABSTRACT

An assembly for selectively performing a clinical chemical test or an ELISA assay including a reagent cartridge with a housing 11 having at least one cavity 12, 13, 14 that contains a reaction or diluting component and having a recess 15 in which a solid phase 20 to which an antigen or antibody can be coupled is inserted into the recess 15 of the housing 11. The assembly also includes at least one measuring cell, wherein a measuring cell is assigned to each reagent cartridge and wherein the reagent cartridge and the measuring cell assigned to it are in a linear assembly in an analytical device.

19 Claims, 6 Drawing Sheets

ASSEMBLY FOR SELECTIVELY
PERFORMING A CLINICAL CHEMISTRY
TEST OR AN ELISA ASSAY, USE OF SAID
REAGENT CARTRIDGE AND ASSEMBLY

CROSS-REFERENCE TO RELATED
APPLICATIONS

This application is a continuation of U.S. application Ser. No. 13/503,276, filed on Jun. 21, 2012, which claims priority to PCT patent application PCT/EP/2010/063732 filed on Sep. 17, 2010; and German patent application DE 051428.7 filed on Oct. 30, 2009, the contents of which are incorporated by reference.

FIELD OF INVENTION

The invention relates to a reagent cartridge for an assembly for selectively performing a clinical-chemical test or an ELISA test.

BACKGROUND OF THE INVENTION

Among experts skilled in the art, analytical devices are known for the automatic determination of clinical chemical as well as immunodiagnostic parameters. The devices for determining clinical chemical parameters must meet different requirements than devices for determining immunological parameters.

Clinical chemical parameters are typically determined in the liquid phase of a sample. At least one reagent is added to the sample that causes a change in optical density. Then the sample is placed in a measuring cell that is horizontally irradiated by an optical sample beam. The reaction temperature normally is 37° C. (=body temperature). The reaction devices must be made of properly resistant material to withstand the often aggressive reagents.

Immunodiagnostic parameters however are determined based on the ELISA principle using a substance coupled to a solid phase.

The reaction temperature typically is room temperature, i.e. 18° C. to 25° C. Preparation and storage of the antigen- or antibody-coupled solid phase is particularly critical for these tests. It is especially important to optimally bind the antigens or antibodies to the solid phase.

EP 1 255 115 A2 therefore proposes an analytical insert for one-time use when performing an ELISA in a fully automated analytical device. The insert is a single-piece molded plastic part comprising multiple cavities. The first cavity accommodates the sample, the other cavities contain reagents for performing the ELISA. The housing also comprises two recesses that are interconnected by a slit. Two interconnected wells that were broken out of a microtiter plate coated with the respective antigen or antibody can be inserted into these recesses.

This solution, however, has several disadvantages. For example, the user has to insert the respective wells into the analytical insert, which is more or less well working depending on the architecture of the recess. There is a risk that the reagents in the other cavities may spill out of the cavities when the user has to apply an adequate compressive force to press the well safely into the analytical insert. There is another risk that the well in the end may not be correctly positioned in the analytical device, which may result in undesirable light refraction and deflection of the sample beam of the photometric device and falsify the analysis. In addition, the analytical insert is very fragile, and just the removal of the safety film from the reagent-filled cavities may bend the insert enough so that it can no longer be inserted into the analytical device.

Another disadvantage is that the analytical insert can only be used in devices for performing immunodiagnostic analyses. If it is desirable to determine clinical chemical parameters at the same time, the user has to insert another completely differently composed sample into another device. This can hardly be done in smaller doctor's offices, since it requires the purchase of one expensive device for analyzing immunodiagnostic values and the purchase of a second expensive device for analyzing clinical chemical parameters.

It is therefore the problem of the invention to overcome these and other disadvantages of prior art and to provide a reagent cartridge that can be produced in an easy and cost-efficient way and is particularly easy to handle by the user. The reagent cartridge shall also be suitable for determining immunodiagnostic and clinical chemical parameters in one and the same sample.

SUMMARY OF THE INVENTION

For a reagent cartridge for an assembly for selectively performing a clinical chemical test or an ELISA test comprising a housing having at least one cavity that contains a reaction or diluting component and having a recess, wherein a solid phase to which an antigen or antibody can be coupled can be inserted into said recess of the housing. The invention provides that the reagent cartridge comprises three cavities wherein the first cavity is either used as a diluting cavity, or contains diluent solution, or contains an additional reagent for performing a clinical chemical test, wherein the second cavity is either used as a diluting cavity, or contains conjugate for performing an ELISA or a detection reagent for performing a clinical chemical test, wherein the third cavity is either used as a diluting cavity, or contains substrate for performing an ELISA, or a detection reagent for performing a clinical chemical test or is empty, and wherein either all cavities of the reagent cartridge are used as diluting cavities and/or are empty or wherein the cavities of the reagent cartridge contain a detection reagent for performing a clinical chemical test, conjugate for performing an ELISA, or substrate for performing an ELISA, or are empty.

It is apparent that it is a particular advantage of the reagent cartridge according to the invention that it is suitable for performing both a clinical chemical test and an immunodiagnostic test in one and the same analytical device. In a first embodiment of the invention, it is preferred that the reagent cartridge is a reagent cartridge for performing a clinical chemical test wherein the first cavity is empty, the second cavity contains a first detection reagent and the third cavity contains a second detection reagent for performing a clinical chemical test. It is also conceivable that the reagent cartridge is a reagent cartridge for performing a clinical chemical test wherein two of the cavities are empty and the third cavity contains a detection reagent for performing a clinical chemical test. It is particularly cost-efficient in manufacturing if the solid phase has neither an antigen nor an antibody bound to it and represents a fourth, empty cavity in the reagent cartridge.

In a second embodiment, the reagent cartridge is a reagent cartridge for performing an immunodiagnostic test wherein the first cavity is empty, the second cavity contains conjugate and the third cavity contains substrate for performing an ELISA, and an antigen or antibody is coupled to the solid phase.

In another embodiment, the reagent cartridge is a reagent cartridge for diluting a sample wherein at least one of the three cavities contains a diluent solution and at least one of the three cavities is used as diluting cavity. It is favorable with respect to cost and manufacturing effort in this case if neither an antigen nor an antibody is bound to the solid phase and that the solid phase is used as a diluting cavity or is empty.

It is another advantage of the invention that the solid phase is made of a different material than the housing. For example, the solid phase can be made of polystyrene. This plastic primarily enhances binding of the desired antigen or antibody to the solid phase. At the same time however, it is not particularly resistant to many reagents needed for performing clinical chemical tests. One can see the benefit gained if the housing consists of another material as mentioned above. For example, it is conceivable that the housing is made of polypropylene, a much more resistant material. It is also ensured in this way that the antigen or the antibody will be coupled to the solid phase safely and lastingly while the reagents for performing clinical chemical tests can still be well stored in the reagent cartridge.

It is therefore advantageous if a reagent is pre-filled in at least one of the cavities while the solid phase is either charged with antibody, or is empty, or is used as diluting cavity.

The invention also relates to the use of a reagent cartridge according to the invention for analyzing a clinical chemical parameter in a sample, the use of a reagent cartridge according to the invention for analyzing a immunodiagnostic parameter in a sample, the use of a reagent cartridge according to the invention as a diluting device, and the use of a reagent cartridge according to the invention for providing additional reagents.

Such a use can be particularly advantageous in a method performed in a fully automated device and comprising the following steps:
  a) Insertion of the reagent cartridges for the analyses to be performed into a holding fixture of the fully automated device;
  b) Insertion of the sample into a sample device of the fully automated device;
  c) Determination of the clinical chemical parameters using a measuring cell that is assigned to the reagent cartridge that is to be used for the analysis of the respective clinical chemical parameter;
  d) Determination of the immunodiagnostic parameters using a measuring cell that is assigned to the reagent cartridge that is to be used for the analysis of the respective immunodiagnostic parameter;
  e) Cleaning or removal of the measuring cells used;
  f) Removal of used reagent cartridges and sample containers.

It is apparent that, in this way, both clinical chemical parameters and immunodiagnostic components of a sample can be determined in one and the same procedure. First of all, the method can be performed in one and the same analytical device. It is therefore no longer necessary to purchase different devices for the analysis of clinical chemical parameters and immunodiagnostic parameters, which means huge cost savings especially for smaller doctor's offices. The special advantage is achieved by determining both the clinical chemical parameters and the immunodiagnostic parameters using a measuring cell and by assigning a reagent cartridge according to the invention to each measuring cell. This is different from the conventional method in which only the clinical chemical parameters are measured using a measuring cell while the immunodiagnostic parameters are measured using a microtiter plate.

Another resulting advantage is that the analytical device that uses the reagent cartridge of the invention needs to comprise only one photometric unit for analyzing both the clinical chemical and the immunodiagnostic parameters. It is also possible to determine several clinical chemical and/or immunodiagnostic parameters of a sample in one and the same analytical device. A physician may therefore proceed as follows to make a diagnosis: First the physician takes a sample of the body fluid to be analyzed from the patient. Then the physician selects reagent cartridges according to the invention depending on the parameters the physician wishes to determine. The physician inserts the reagent cartridges for each of the parameters into the analytical device and starts the method according to the invention. This method will provide the various desired clinical chemical and immunodiagnostic parameters on which the physician can base the diagnosis.

It is apparent that the use of the reagent cartridges according to the invention in such a method provides the advantage that a dedicated reagent cartridge is inserted into a holding fixture of the analytical device for each clinical chemical and/or immunodiagnostic parameter to be determined, and the respective reagent cartridge contains the detection reagents required for the respective test in its cavities. It is preferred that all reagent cartridges used for analyzing clinical chemical parameters contain at least one detection reagent and that reagent cartridges used for analyzing immunodiagnostic parameters contain a first cavity with conjugate, a second cavity with substrate, and a solid phase. It is apparent that the reagent cartridge according to the invention facilitates this is in a particularly advantageous manner.

Determination of immunodiagnostic parameters may, for example, include the following steps:
  a) The pipetting device picks up the enzyme conjugate from a first cavity of the reagent cartridge intended for performing the immunodiagnostic analysis and a quantity of the sample.
  b) The pipetting device dispenses enzyme conjugate and sample onto the solid phase of the reagent cartridge.
  c) The solid phase is incubated with conjugate and sample.
  d) Excessive conjugate and sample is removed by washing the solid phase.
  e) The pipetting device picks up the substrate from a second cavity of the reagent cartridge intended for performing the immunodiagnostic analysis.
  f) The substrate is dispensed from the pipetting device onto the solid phase.
  g) The substrate is incubated on the solid phase.
  h) The pipetting device picks up the reacted substrate.
  i) The reacted substrate is dispensed from the pipetting device into the measuring cell.
  j) The concentration of the reacted substrate is measured using the measuring device.

Alternatively, conjugate and sample can be picked up in two separate steps and pipetted onto the solid phase. For example, the pipetting device can first pick up the conjugate and dispense it onto the solid phase, then the pipetting device picks up the sample and dispenses it onto the solid phase. It is, of course, also conceivable that the sample is picked up first and dispensed onto the solid phase, then the conjugate.

The steps a) through g) correspond to the common steps of performing an ELISA. When conjugate and sample are jointly dispensed onto the solid phase, the immunological parameter to be detected, e. g. a specific peptide, antibody, or other protein, binds to its binding partner that is coupled to the solid phase—a matching antibody, antigen or the like. The conjugate however contains a matching enzyme complex that consists of a binding partner and an enzyme coupled to the binding partner. The binding partner also binds to the parameter to be detected. The entire complex of parameter, binding partner, and enzyme is immobilized on the solid phase in this way. Excess complex and sample are removed or washed out in the next step. The substrate solution added then contains a substrate that is specific to the enzyme immobilized in this way on the solid phase. This substrate is reacted with the enzyme, which causes a color change and thus a defined change in optical density at a specific wavelength.

It is the special advantage of such a method when using the reagent cartridge according to the invention that the substrate reaction is ended in that the entire substrate solution that now contains reacted and non-reacted substrate is removed from the solid phase and re-pipetted into a measuring cell for analysis. This makes it possible to determine a multitude of different parameters—primarily immunodiagnostic ones but also clinical chemical ones—always using the same assembly of reagent cartridges and measuring cells. The concentration of the respective parameter can be determined in always the same sequence of steps using the measuring cell and a single photometric unit.

It is another advantage that there is no need to provide a stopping solution as an additional component that would otherwise typically be used to end the enzyme substrate reaction as defined. The reaction is ended here by simply removing the partially reacted substrate solution and re-pipetting it into the measuring cell. Since the enzymes immobilized on the solid phase remain on the solid phase and are not taken along into the measuring cell. no more substrate will be reacted as soon as the solutions is removed from the solid phase.

It is also favorable to determine the immunodiagnostic parameters using the reagent cartridge according to the invention at a temperature between 27° C. and 39° C., preferably at a temperature of 37° C. This special adjustment of the temperature conditions of the ELISA tests makes it possible that clinical chemical and immunodiagnostic parameters can be determined in any sequence one after the other without having to change the temperature of the analytical device use, which would otherwise involve long cooling and heating phases. Another advantage of raising the temperature is that the temperature is significantly above the regular room temperature. It is therefore irrelevant where the analyzer is placed; the temperature at which the test is performed is always kept constant. The reaction kinetics are always the same as well. This makes test results more repeatable. It is also not required to establish a standard curve for each test as would otherwise be common with ELISA. The components provided in the reagent cartridges according to the invention for performing an immunodiagnostic test are therefore tuned to be of particular advantage when performing the test at a temperature of 37° C.

The invention further relates to an assembly for selectively performing a clinical chemical or ELISA test comprising an analytical device, at least one reagent cartridge and at least one measuring cell, wherein the reagent cartridge is a reagent cartridge of the invention and wherein a measuring cell is assigned to each reagent cartridge, and the reagent cartridge and the measuring cell 30 assigned to it are in a linear Change(s) assembly in the analytical device.

It is advantageous in such an assembly that the analytical device comprises a sample receptacle, a holding fixture for the reagent cartridges and for the measuring cells, and a pipetting device, and that the analytical device comprises an optical unit and a washing unit. It is also favorable if sample receptacle and washing unit are separate from the holding fixture and if the holding fixture is a carousel wherein the reagent cartridges and measuring cells are arranged on the radii of the carousel and wherein the measuring cells are arranged on the outer ends of these radii.

Other features, details, and advantages of the invention can be derived from the wording of the claims and from the following description of embodiments with reference to the figures.

DETAILED DESCRIPTION OF THE INVENTION

Figure 1:
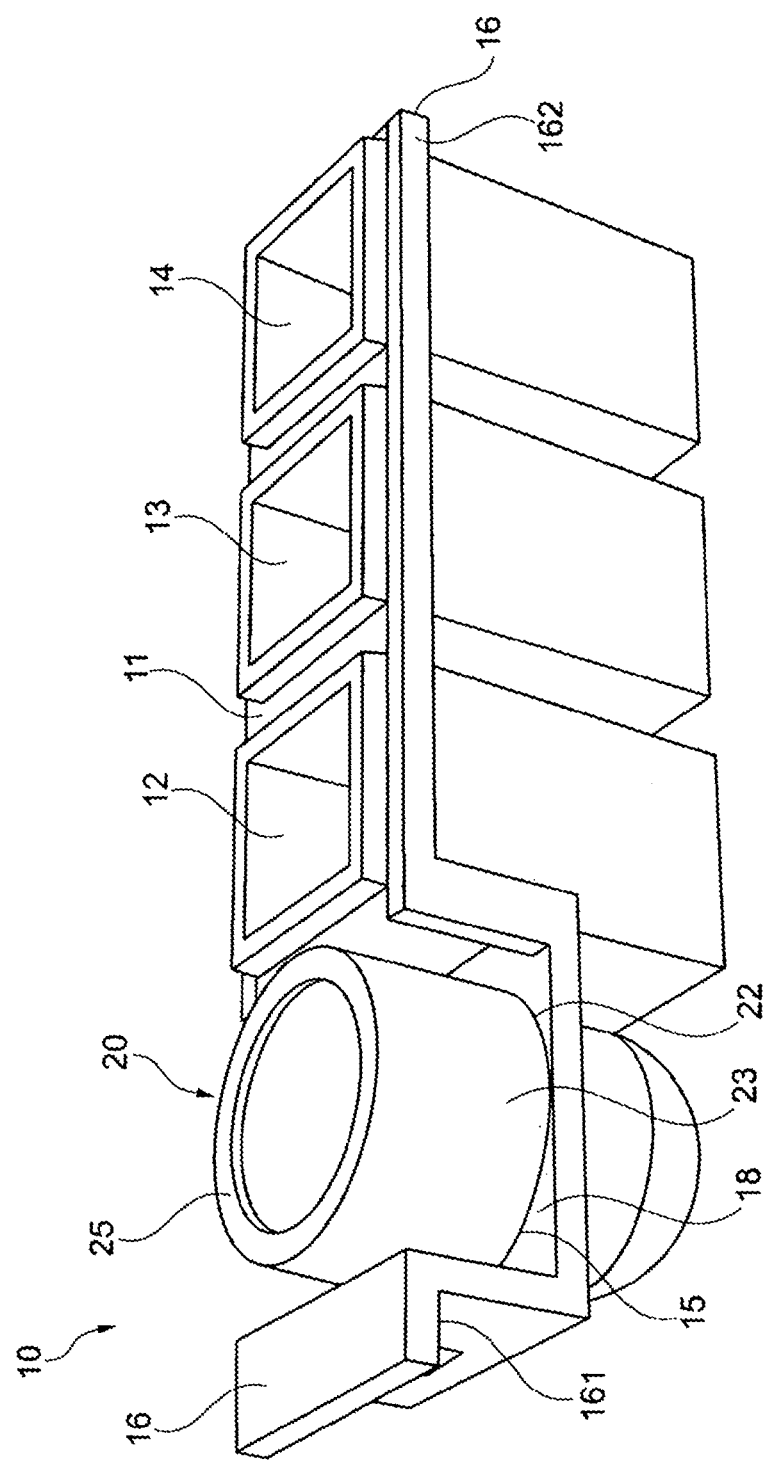
FIG. 1 shows a reagent cartridge according to the invention.
Figure 2:
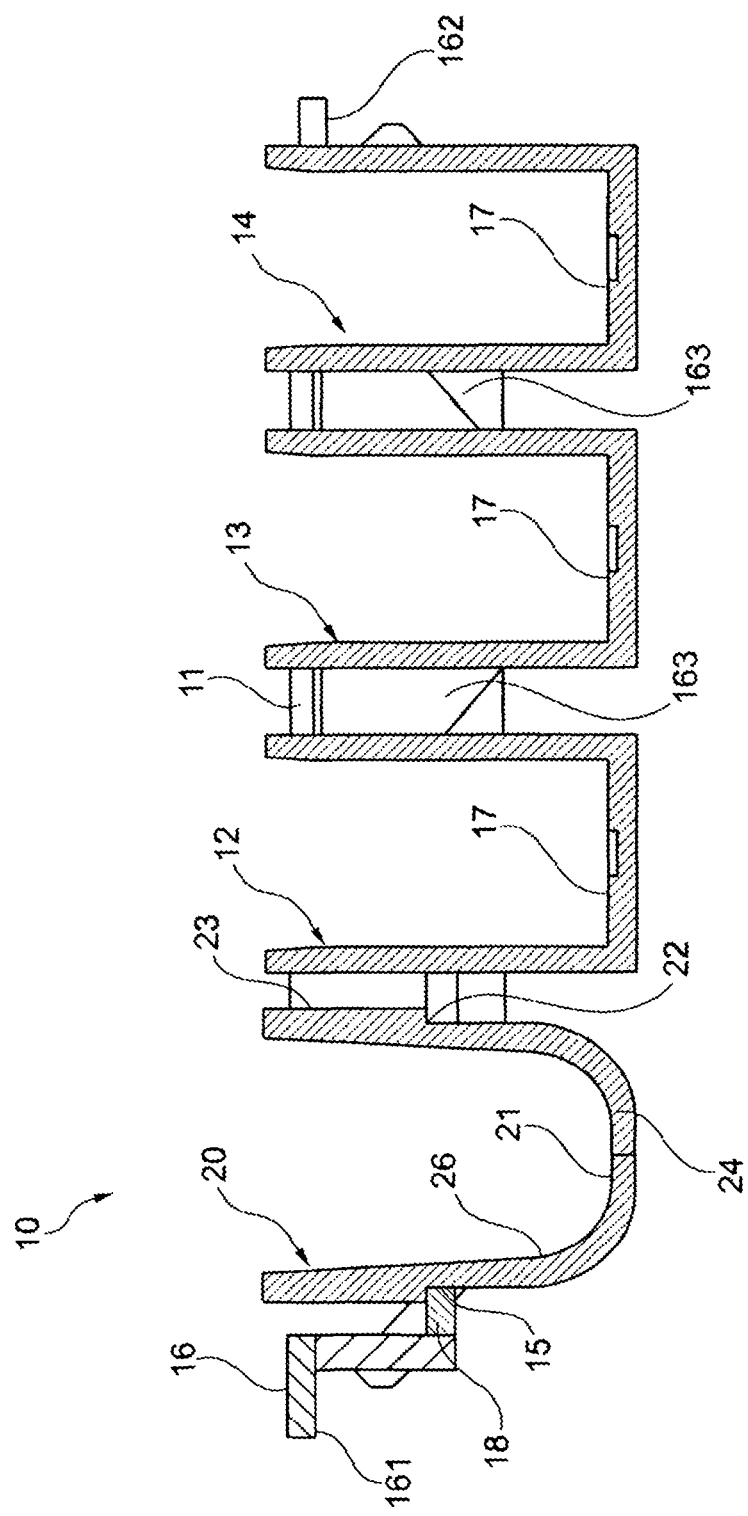
FIG. 2 shows a cross section through the reagent cartridge of FIG. 1.
Figure 3:
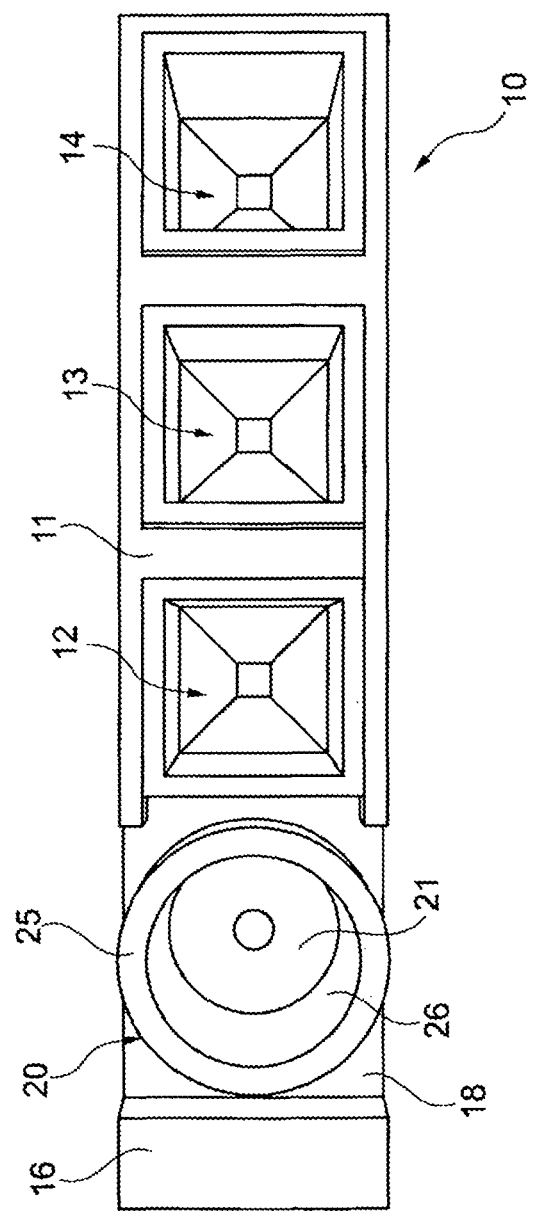
FIG. 3 shows a top view of the reagent cartridge of FIG. 1.

The reagent cartridge 10 shown in FIGS. 1, 2, and 3 consists of a housing 11 in which three cavities 12, 13, 14 are formed. The housing 11 also comprises a recess 15 into which a solid phase 20 can be inserted. The solid phase 20 has the form of a single well from a microtiter plate and is preferably made of polystyrene while the housing 11 and the cavities 12, 13, 14 are made of a resistant material matched to the reagents of the clinical chemical test, such as polypropylene.

The housing 11 has a main level 16 with a front end 161 and a rear end 162. When the reagent cartridge 10 is inserted into the analytical device, the bottom sides of its front and rear ends 161, 162 rest on the analytical device and thus secure it in its position (see also FIG. 5). It can be seen that the upper openings of the cavities 12, 13, 14 are located along the upper, main level 16. The recess 15 that is to accommodate the solid phase 20 is formed at a deeper level 18.

The solid phase 20 has been inserted into the recess 15 in FIGS. 1 and 2. It has a peripheral rim 23 with a projection 22 extending on its end. This projection 22 rests on deeper level 18 which prevents it from slipping through the recess 15. The upper rim 25 of the solid phase 20 is level with the upper rims of the cavities 12, 13, and 14. This makes yet another special advantage of the reagent cartridge 10 apparent in that it can be delivered to the user with the solid phase already prepared and inserted. In addition, the solid phase 20 is reliably and safely stored in the housing 11 of the reagent cartridge 10. This effectively prevents errors that could result when the user inserts the solid phase 20 incorrectly into the housing 11. It not only makes the use of the cartridge much easier but results in improved reliability of the measuring results obtained using the reagent cartridge 10.

It can be seen, especially in FIG. 2, that supporting webs 163 can be formed among the cavities 12, 13, and 14 that ensure a stable overall structural design of the reagent cartridge 10. The supporting webs 163 primarily ensure that the reagent cartridge 10 will always be positioned level when inserted into the analytical device and will not bend, e.g. due to influences from the pipetting device.

If the reagent cartridge 10 is intended for performing an immunodiagnostic test, a respective antigen or antibody suitable for the test can be coupled to the inner wall 21 of the bottom 24 and the side walls 26 of the solid phase 20. If the reagent cartridge 10 is intended for performing a clinical chemical test, for providing additional reagents, or as a diluent cartridge, the solid phase 20 can be used without an antigen or antibody coupled to it.

FIGS. 4a to 4d show various options according to the invention for filling the reagent cartridge 10 and providing it in filled condition to a user.

Figure 4A:
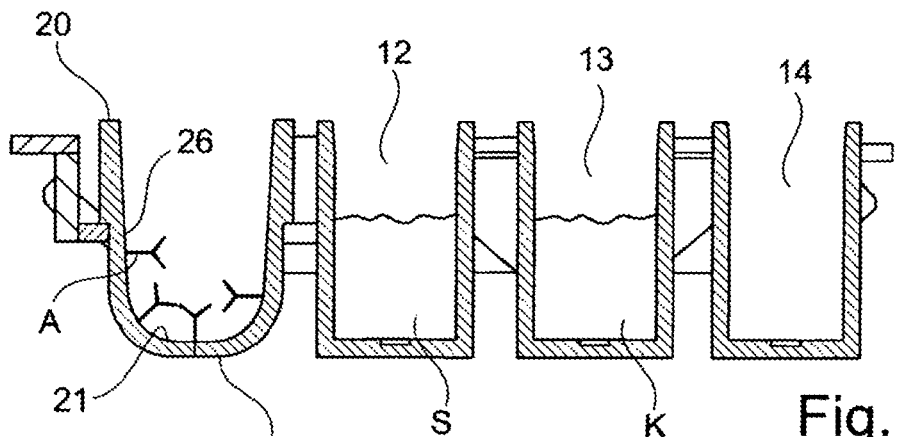
FIG. 4a shows the use of the reagent cartridge from FIG. 2 to perform an ELISA.

The first cavity 14 of the reagent cartridge 10 shown in FIG. 4a is empty and can be used flexibly for various applications. The second cavity 13 contains an enzyme conjugate K and the third cavity contains a substrate solution S. An antigen or antibody A is coupled to the bottom 24 and the side walls 26 of the solid phase 20.

For performing an ELISA using the reagent cartridge, a pipetting device (not covered by the patent) is used to add enzyme conjugate K and the sample that is stored in a separate container outside the device (not shown) to the solid phase 20. This can be done by either picking up the enzyme conjugate K and the sample P simultaneously or in two separate pipetting steps. If the immunological component to be detected is contained in the sample, it will bind to the antigen or antibody A that is immobilized on the solid phase 20. The immunological component also bind the enzyme conjugate K. In this way, both the component to be detected and the enzyme contained in the enzyme conjugate K are also immobilized on the solid phase 20. Excess sample and enzyme conjugate K will then be removed, and the substrate solution S is added to the solid phase 20. The substrate contained in the substrate solution S is reacted by the enzyme of the enzyme conjugate K that is immobilized on the solid phase 20 and causes a photochemically detectable change in the optical density of the solution contained in the solid phase 20.

Figure 4B:
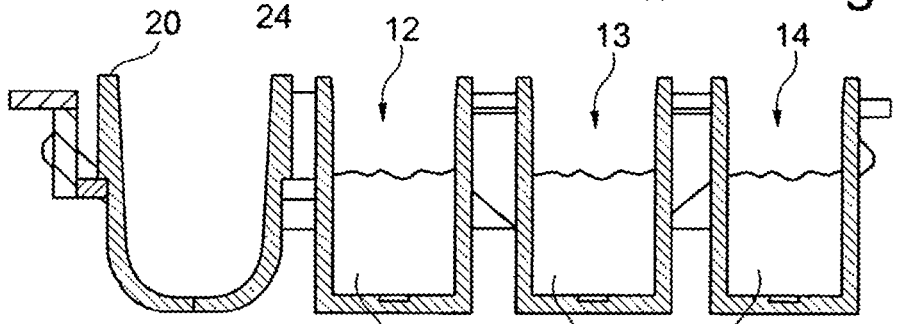
FIG. 4b shows the use of the reagent cartridge from FIG. 2 to perform a clinical chemical test.

As shown in FIG. 4b, the reagent cartridge according to the invention 10 is not charged with enzyme conjugate and substrate solution for performing a clinical chemical test but is filled with a first reagent R1 and, if required for the specific test, with two or more other reagents R2, R3 in the cavities 12, 13, and 14. It is instead conceivable that the solid phase 20 also accommodates a reagent for performing the test. One can see that the manifold uses of the reagent cartridge 10 according to the invention pose a particular advantage. For example, different solid phases 20 can be inserted into the housing 11. They may consist of one of the materials mentioned or of a third material suitable for the respective application.

If more than three or four reagents are needed for a specific clinical chemical test, the reagent cartridge 10 of the invention can be used to accommodate additional reagents.

Figure 4C:
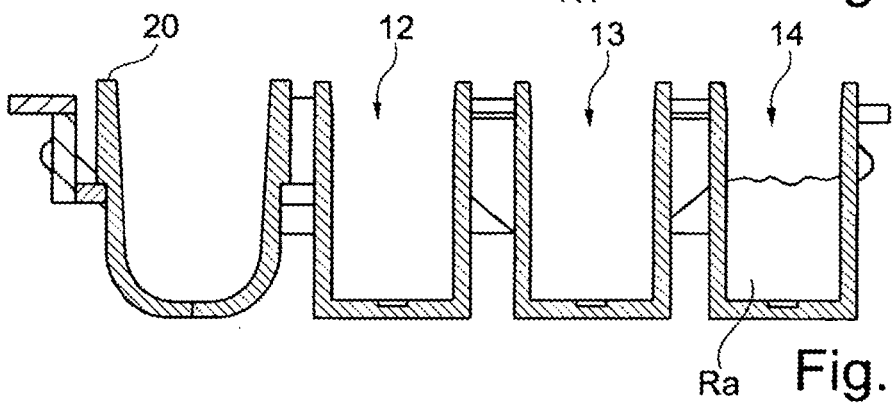
FIG. 4c shows the use of the reagent cartridge from FIG. 2 as a diluent cartridge.

For performing the test, the reagent cartridge 10 shown in FIG. 4c is simply inserted into the analytical device next to the actual reagent cartridge 10 as shown in FIG. 4b.

Figure 4D:
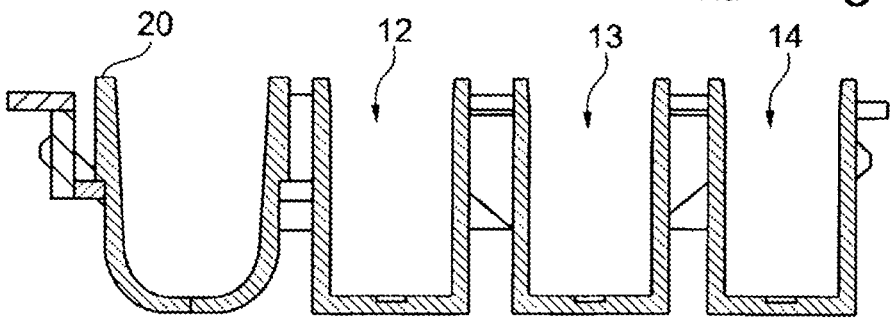
FIG. 4d shows the use of the reagent cartridge from FIG. 2 for providing additional reagents.

If for one of the desired tests to be performed it is necessary to dilute the sample to be analyzed, another reagent cartridge 10 of the invention may be used as diluent cartridge. As shown in FIG. 4d, the cavities 12, 13, 14 and the solid phase 20 may be empty in such a cartridge while the diluent solution is added from a container that is provided separately on the analytical device. It is also conceivable that a diluent solution is already pre-filled at defined volumes in the cavities 12, 13, 14 serving as diluent cavities.

Figure 5:
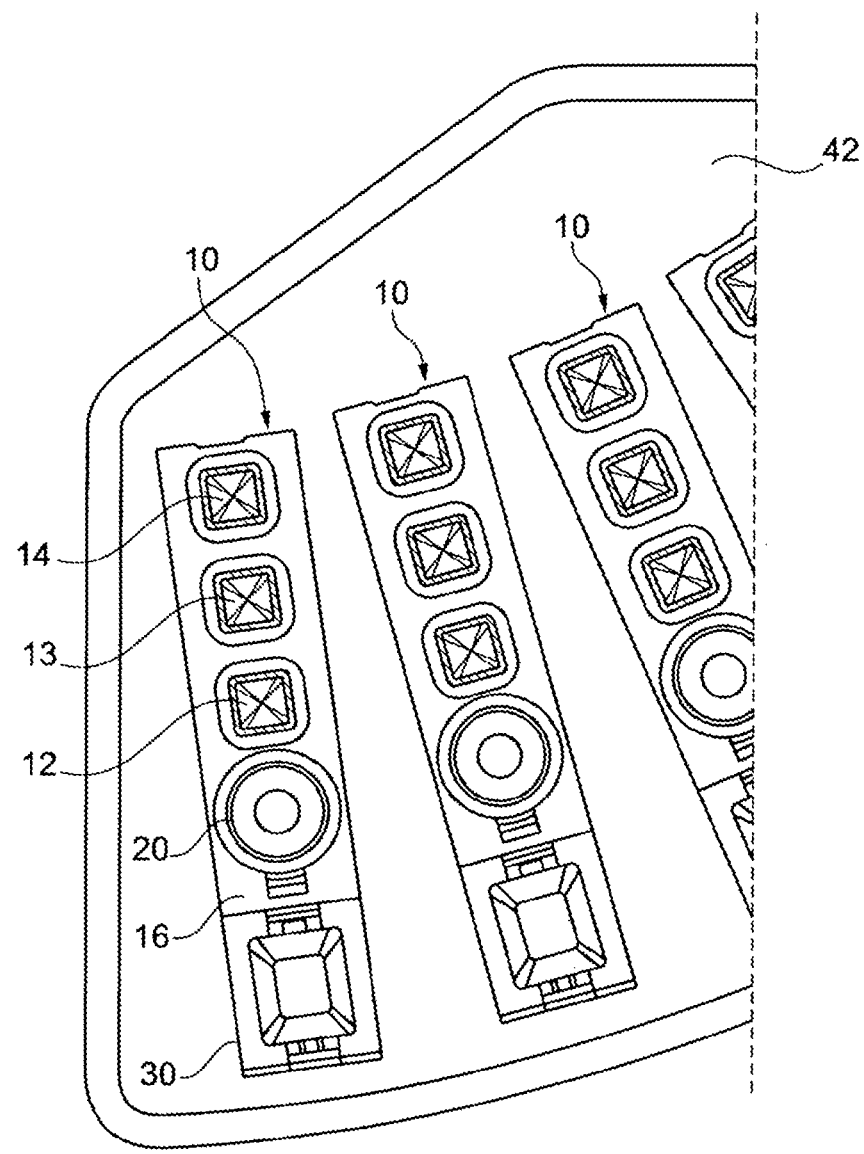
FIG. 5 shows the use of a reagent cartridge according to the invention in a fully automated device.

It can be seen in FIG. 5 how various reagent cartridges 10 according to the invention are used in a fully automated analytical device 40. These cartridges are inserted into a carousel-shaped holding fixture 42 of the analytical device 40 such that their cavities 12, 13, 14 and the solid phase 20 are always level with a measuring cell 30 assigned to the respective reagent cartridge 10 and used for the photometric analysis of the test results.

Figure 6:
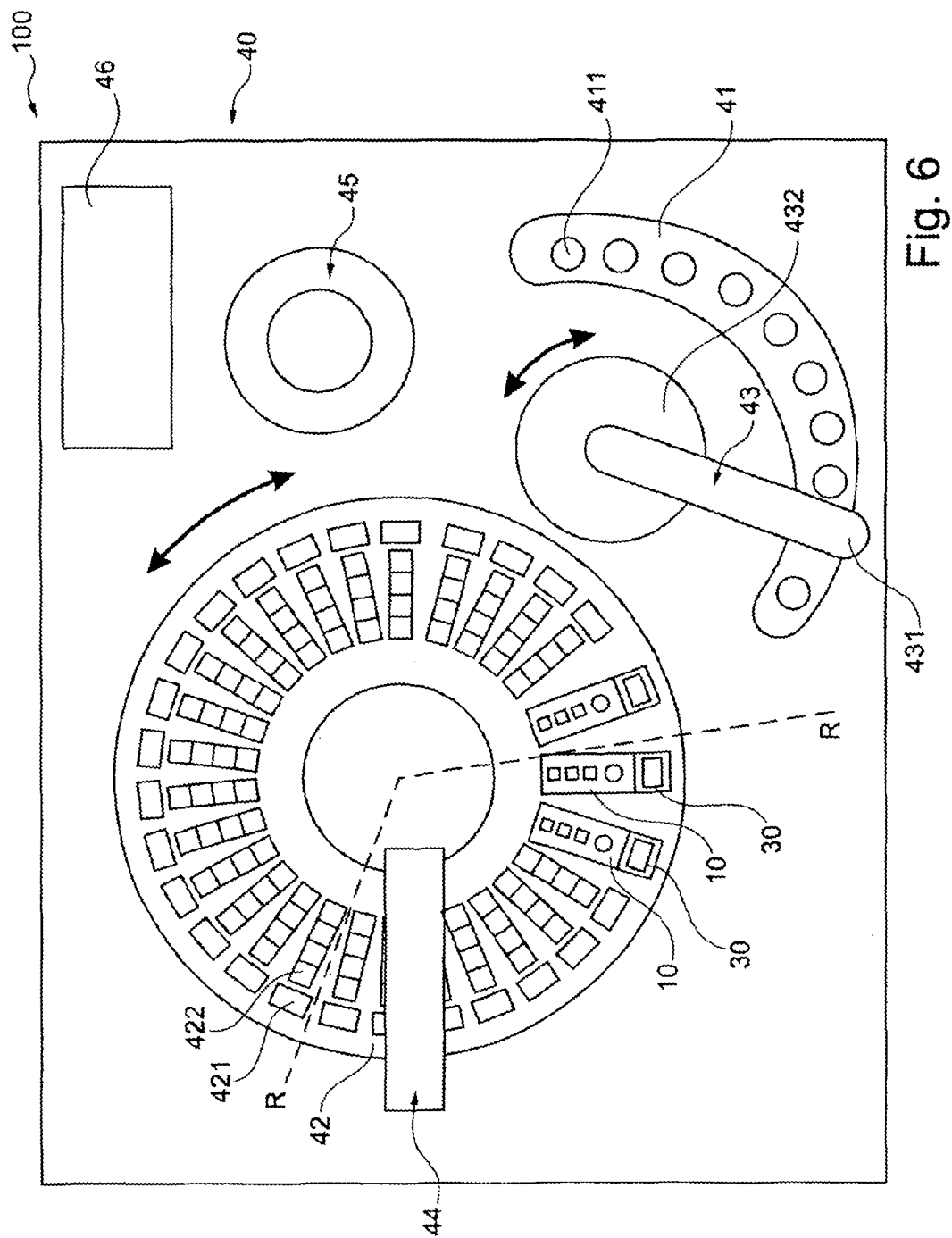
FIG. 6 shows a diagrammatic view of an assembly for selectively analyzing clinical chemical and immunodiagnostic parameters in which reagent cartridges of the invention are used.

FIG. 6 shows a general view of the analytical device 40 and the assembly 100. The analytical device 40 consists of a holding fixture 42, a sample receptacle 41, a pipetting device 43, an optical unit 44, and a washing unit 45.

The holding fixture 42 comprises both cavities 421 for receiving measuring cells 30 and cavities 422 for receiving reagent cartridges 10 according to the invention. It can be seen that there are one cavity 421 for receiving a measuring cell 30 and one cavity for receiving a reagent cartridge 10 on a common radius R of the holding fixture 42, wherein the cavity 421 for receiving the measuring cell 30 is located on the outer end of the radius R.

The sample receptacle 41 comprises cavities 411 as well. A vial or cup containing the sample to be examined can be inserted into these cavities. It can be seen that the sample receptacle 41 is separate from the holding fixture 42.

The pipetting device 43 consists of a pivotable robot arm 431 that is mounted onto a pivoting mechanism 432. A pipette that can be washed in the washing unit 45 between pipetting steps, if required, is attached to the bottom side of the robot arm 431.

It can be seen that the robot arm 431 can be pivoted among various positions over the sample receptacle 41 and holding fixture 42 that it can target and pick up either reagents from the inserted reagent cartridges 10 or samples from the sample receptacle 41 and add them selectively to another cavity 12, 13, 14 of a reagent cartridge 10, to the solid phase 20, or into the measuring cell 30.

In the embodiment shown, measuring cells 30 and reagent cartridges 10 have been inserted into some of the cavities 421, 422 of the holding fixture 42. This reveals a particular advantage of the invention. It is not required that the entire holding fixture 42 is equipped. Instead, a physician who wishes to use the assembly for a fast analysis of a patient's sample would proceed as follows:

The physician thinks of the parameters he would like to determine for his diagnosis and takes the patient's sample. He switches on the analytical device 40 that will heat up to a constant operating temperature of 37° C. Then he or another person who performs the test inserts the sample into the cavity 411 of the sample receptacle 41 and the reagent cartridges 10 and measuring cells 30 for the respective parameters to be determined into the cavities 421, 422 of the holding fixture 42. The person performing the test will then start the analysis using a computer control unit 46. The computer control unit 46 may either be an integral part of the analytical device 40 as in the embodiment shown here or an external computer connected to the analytical device 40.

The robot arm 43 then picks up the reagents and samples according to the method described above and pipettes them back and forth until the measuring cell 30 that is assigned to the reagent cartridge 10 for the respective parameter to be determined contains an optically analyzable solution. The holding fixture 42 is pivoted such that the contents of the measuring cell 30 can be analyzed in the optical unit 44. It is preferred that the optical unit 44 is a photometric unit that determines the optical density OD of the solution in the measuring cell 30 at a specific wavelength defined for the respective test and passes the result on to the computer for output.

It is particularly preferred that the following procedure is followed when analyzing immunodiagnostic parameters using such an assembly 100 and the respective analytical device 40:

a) The pipetting device 43 picks up enzyme conjugate K from a first cavity 13 of the reagent cartridge 10 intended for performing the immunodiagnostic analysis and picks up sample from the sample inserted into a cavity 411 of the sample receptacle 41.

b) The pipetting device 43 dispenses enzyme conjugate K and sample onto the solid phase 20 of the reagent cartridge 10.

c) The solid phase 20 is incubated with enzyme conjugate K and sample.

d) Excessive enzyme conjugate K and sample is removed by washing the solid phase 20.

e) The pipetting device 43 picks up the substrate S from a second cavity 12 of the reagent cartridge 10 intended for performing the immunodiagnostic analysis.

f) The substrate S is dispensed from the pipetting device 43 onto the solid phase 20.

g) The substrate S is incubated on the solid phase 20.

h) The pipetting device 43 picks up the reacted substrate S.

i) The reacted substrate S is dispensed from the pipetting device 43 into the measuring cell 30.

j) The concentration of the reacted substrate S is measured using the optical unit 44.

Conjugate K and sample may of course be picked up in any sequence as described above and added to the solid phase 20.

The solid phase is washed by either flushing washing solution from the washing station 45 into the solid phase or providing another washing facility (not shown).

The invention is not limited to one of the embodiments described above but can be modified in manifold ways.

For example, the solid phase 20 comprises a round bottom while the cavities 12, 13, 14 have a flat bottom 17 in the embodiments shown above. Of course, another bottom architecture is conceivable.

If the reagent cartridge 10 is used as a diluent cartridge, it is conceivable that one or two of the cavities 12, 13, 14 are filled with diluent solution while the other cavities 12, 13, 14 are empty such that the actual diluting process can be performed in them by adding defined volumes of diluent solution and sample.

Any and all features and advantages from the claims, the description and the figures including design details, spatial assemblies and procedural steps can be essential to the invention both in their own right and in the most varied combinations.

In a reagent cartridge for an assembly for selectively performing a clinical chemical test or an ELISA test, comprising a housing 11 having at least one cavity 12, 13, 14 that contains a reaction or diluting component and comprises a recess 15, wherein a solid phase 20 is inserted into the recess 15 of the housing 11 to which an antigen or antibody can be coupled, it is particularly advantageous if the reagent cartridge 10 comprises three cavities 12, 13, 14, wherein the first cavity 14 is either used as diluting cavity or contains diluent solution, or contains an additional reagent for performing a clinical chemical test, wherein the second cavity 13 is either used as diluting cavity, or contains enzyme conjugate K for performing an ELISA, or contains a detection reagent R1, R2, R3, Ra for performing a clinical chemical test, wherein the third cavity 12 is either used as diluting cavity, or contains substrate S for performing an ELISA, or contains a detection reagent R1, R2, R3, Ra for performing a clinical chemical test, or is empty, and wherein either all cavities 12, 13, 14 of the reagent cartridge 10 are used as diluting cavities and/or contain diluent solution, and/or are empty, or wherein the cavities 12, 13, 14 of the reagent cartridge 10 contain a detection reagent R1, R2, R3, Ra for performing a clinical chemical test, enzyme conjugate K for performing an ELISA, or substrate S for performing an ELISA, or are empty.

If the reagent cartridge 10 is a reagent cartridge for performing a clinical chemical test, it is useful if the first cavity 14 is empty, the second cavity 13 contains a first detection reagent R1, and the third cavity 12 contains a second detection reagent R2 for performing a clinical chemical test. It is also favorable—if the reagent cartridge 10 is a reagent cartridge for performing a clinical chemical test—if two of the cavities 12, 13 are empty and the third cavity 14 contains a detection reagent Ra, R3 for performing a clinical chemical test. It is easy to see the advantage that the solid phase 20 has neither an antigen nor an antibody bound to it and represents a fourth, empty cavity of the reagent cartridge 10.

If the reagent cartridge 10 is a reagent cartridge for performing an immunodiagnostic test, it is useful that the first cavity 14 is empty, the second cavity 13 contains enzyme conjugate K, and the third cavity 12 contains substrate S for performing an ELISA, wherein an antigen or antibody A is coupled to the solid phase 20.

If the reagent cartridge 10 is a reagent cartridge for diluting a sample, it is useful that at least one of the three cavities 12, 13, 14 contains a diluent solution and at least one of the three cavities 12, 13, 14 is used as diluting cavity. It is favorable in this case if the solid phase 20 is neither bound to an antigen nor to an antibody and that the solid phase 20 is used as diluting cavity or is empty.

It is yet another apparent particular advantage that the solid phase 20 is made of a different material than the housing 11. For example, it is favorable if the solid phase 20 is made of polystyrene.

It is apparent that it is favorable for a reagent cartridge 10 according to the invention that a reagent R1, R2, R3, Ra, K, S is pre-filled in at least one of the cavities 12, 13, 14 while the solid phase 20 is either charged with antibody A, is empty or is used as diluting device.

Another apparent advantage is the use of a reagent cartridge 10 according to the invention for analyzing a clinical chemical parameter in a sample, the use of a reagent cartridge 10 according to the invention for analyzing a immunodiagnostic parameter in a sample, the use of a reagent cartridge 10 according to the invention as a diluting device, and the use of a reagent cartridge 10 according to the invention for providing additional reagents.

The invention further relates to an assembly 100 for selectively performing a clinical chemical or an ELISA test comprising an analytical device 40, at least one reagent cartridge 10, and at least one measuring cell 30, wherein the reagent cartridge is a reagent cartridge of the invention and wherein a measuring cell is assigned to each reagent cartridge, and the reagent cartridge and the measuring cell 30 assigned to it are in a linear assembly in the analytical device. It is useful if such an analytical device 40 comprises a sample receptacle 41, a holding fixture 42 for the reagent cartridges 10 and for the measuring cells 30, and a pipetting device 43, and if the analytical device 40 comprises an optical unit 44 and a washing unit 45. It is advantageous if the sample receptacle 41 and the washing unit 45 are separate from the holding fixture 42 and if the holding fixture 42 is a carousel wherein the reagent cartridges 10 and measuring cells 30 are arranged on the radii R of the carousel and wherein the measuring cells 30 are arranged on the outer ends of the radii R.

| List of reference symbols | |
|---|---|
| A | Antigen/antibody |
| K | Enzyme conjugate |
| R | Radius |
| R1 | Reagent |
| R2 | Reagent |
| R3 | Reagent |
| Ra | Reagent |
| S | Substrate solution |
| 10 | Reagent cartridge |
| 11 | Housing |
| 12 | Cavity |
| 13 | Cavity |
| 14 | Cavity |
| 15 | Recess |
| 16 | Main level |
| 161 | Front end |
| 162 | Rear end |
| 163 | Supporting web |
| 17 | Bottom |
| 18 | Deeper level |
| 20 | Solid phase |
| 21 | Inner wall |
| 22 | Projection |
| 23 | Rim |
| 24 | Bottom |
| 25 | Rim |
| 26 | Side wall |
| 30 | Measuring cell |
| 40 | Analytical device |
| 41 | Sample receptacle |
| 411 | Cavity |
| 42 | Holding fixture |
| 421 | Cavity |
| 422 | Cavity |
| 43 | Pipetting device |
| 431 | Robot arm |
| 432 | Pivoting mechanism |
| 44 | Optical unit |
| 45 | Washing unit |
| 46 | Computer control unit |

What is claimed:

1. An assembly for selectively performing a clinical chemical test or an ELISA test comprising:
   an analytical device, wherein the analytical device comprises a holding fixture and an optical unit, and is adapted to control the temperature of the holding fixture at between 27° C. and 39° C.;
   at least one reagent cartridge including:
      a housing defining three cavities and a recess, and
      a solid phase to which an antigen or antibody can be coupled, wherein the solid phase is positioned into the recess of the housing,
      wherein the first cavity is either used as a diluting cavity or contains diluent solution, or contains an additional reagent for performing a clinical chemical test, or is empty,
      wherein the second cavity is either used as a diluting cavity, or contains enzyme conjugate K for performing an ELISA, or contains a detection reagent for performing a clinical chemical test, or is empty,
      wherein the third cavity is either used as a diluting cavity, or contains substrate for performing an ELISA, or contains a detection reagent for performing a clinical chemical test, or is empty, and
      wherein either all cavities of the reagent cartridge are used as diluting cavities and/or contain diluent solution, and/or are empty, or wherein the cavities of the reagent cartridge contain a detection reagent for performing a clinical chemical test, enzyme conjugate for performing an ELISA, or substrate for performing an ELISA, or are empty, and
   at least one measuring cell,
   wherein the holding fixture is a carousel and comprises a plurality of cavities for receiving a reagent cartridge and an equal number of cavities for receiving a measuring cell,
   wherein each of the plurality of cavities for receiving a reagent cartridge is arranged in a linear assembly with one of the plurality of cavities for receiving a measuring cell along common radii of the carousel, and
   wherein the holding fixture is adapted to place the at least one measuring cell in a position to be measured by the optical unit.

2. The assembly according to claim 1, wherein the reagent cartridge is a reagent cartridge for performing a clinical chemical test wherein the first cavity is empty, the second cavity contains a first detection reagent, and the third cavity contains a second detection reagent for performing a clinical chemical test.

3. The assembly according to claim 1, wherein the reagent cartridge is a reagent cartridge for performing a clinical chemical test wherein two of the cavities are empty and the third cavity contains a detection reagent for performing a clinical chemical test.

4. The assembly according to claim 1, wherein the solid phase has neither an antigen nor an antibody bound to it and represents a fourth cavity of the reagent cartridge which is empty.

5. The assembly according to claim 1, wherein the reagent cartridge is a reagent cartridge for performing an immunodiagnostic test, wherein the first cavity is empty, the second cavity contains enzyme conjugate, and the third cavity contains substrate for performing an ELISA, wherein an antigen or antibody is coupled to the solid phase.

6. The assembly according to claim 1, wherein the reagent cartridge is a reagent cartridge for diluting a sample, wherein at least one of the three cavities contains a diluent solution and at least one of the three cavities is used as a diluting cavity.

7. The assembly according to claim 6, wherein neither an antigen nor an antibody is bound to the reagent cartridge and in that the solid phase is used as a diluting cavity or is empty.

8. The assembly according to claim 1, wherein the solid phase is made of a different material than the housing.

9. The assembly according to claim 1, wherein the solid phase is made of polystyrene.

10. The assembly according to claim 1, wherein a reagent is pre-filled in at least one of the cavities.

11. The assembly according to claim 1, wherein the solid phase is either charged with antibody, is empty, or is used as a diluting device.

12. Use of the assembly according to claim 1 for analyzing a clinical chemical parameter in a sample.

13. Use of the assembly according to claim 1 for analyzing an immunodiagnostic parameter in a sample.

14. The assembly according to claim 1, wherein the analytical device comprises a sample receptacle, and a pipetting device.

15. The assembly according to claim 14, wherein the analytical device comprises a washing unit.

16. The assembly according to claim 15, wherein the sample receptacle and the washing unit are separate from the holding fixture.

17. The assembly according to claim 1, wherein the plurality of cavities for receiving a measuring cell are arranged on the outer ends of the common radii.

18. The assembly according to claim 1, wherein the reagent cartridge includes a supporting web extending between adjacent pairs of the three cavities.

19. The assembly according to claim 1, wherein the analytical device is adapted to control the temperature of the holding fixture at 37° C.

\* \* \* \* \*